United States Patent [19]

Andre et al.

[11] Patent Number: 4,713,485
[45] Date of Patent: Dec. 15, 1987

[54] PROCESS FOR PREPARING α-HYDROXY-ALKANOIC ACIDS AND COMPOUNDS OBTAINED BY THIS PROCESS

[75] Inventors: Jean-Daniel Andre, Sisteron; Pierre-Jean Grossi, Aramon; Alain Heymes, Sisteron, all of France; Giovanni V. Manzaroli, Milan, Italy

[73] Assignee: SANOFI and Industria Chimica Prodotti FRANCIS S.p.A., Paris, France

[21] Appl. No.: 800,228

[22] Filed: Nov. 21, 1985

[30] Foreign Application Priority Data

Nov. 29, 1984 [FR] France ............... 84 18201

[51] Int. Cl.$^4$ ............................................. C07C 59/48
[52] U.S. Cl. ....................................... 562/470; 562/508
[58] Field of Search ........................ 562/471, 470, 508

[56] References Cited

FOREIGN PATENT DOCUMENTS

| 2040218 | 2/1972 | Fed. Rep. of Germany | 562/470 |
| 46-34698 | 11/1971 | Japan | 562/470 |
| 0235009 | 1/1969 | U.S.S.R. | 562/470 |

*Primary Examiner*—Paul J. Killos
*Attorney, Agent, or Firm*—Bacon & Thomas

[57] ABSTRACT

The invention relates to a process for preparing α-hydroxy-alkanoic acids of general formula:

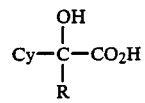

in which R represents hydrogen or a lower alkyl radical and Cy represents phenyl or a heterocyclic radical, both radicals optionally comprising one or more substituents selected from the group consisting of lower alkyl, lower alkenyl, lower alkynyl radicals and halogen atoms, process which comprises the treatment of an α,α-dihalogenated ketone of general formula:

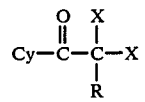

in which R and Cy have the same meaning as above and X represents chlorine, bromine or iodine, in the presence of an aqueous solution of an alkali metal hydroxide and a non polar organic solvent selected from an aromatic or alicyclic hydrocarbon, the treatment being carried out at a temperature between the boiling temperature of the reaction medium at atmospheric pressure and 240° C. under pressure and the alkali metal so formed is then acidified to obtain the desired acid.

9 Claims, No Drawings

PROCESS FOR PREPARING α-HYDROXY-ALKANOIC ACIDS AND COMPOUNDS OBTAINED BY THIS PROCESS

This invention relates to a novel process for preparing α-hydroxy-alkanoic acids and to the compounds obtained by this process.

More particularly, the invention concerns a novel process for preparing α-hydroxy-alkanoic acids of general formula:

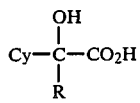

in which R represents hydrogen or a lower alkyl radical and Cy represents a phenyl or a heterocyclic radical, both radicals optionally comprising one or more substituents selected from the group consisting of lower alkyl, lower alkenyl, lower alkynyl radicals and halogen atoms such as chlorine or bromine.

In the present context, the terms cited hereunder have the following meaning:

"lower alkyl" designates saturated aliphatic hydrocarbon radicals having up to 4 carbon atoms, such as methyl, ethyl, n-propyl, isopropyl, n-butyl, isobutyl or tert-butyl;

"lower alkenyl" designates unsaturated aliphatic hydrocarbon radicals comprising one or two double bonds and having from 2 to 4 carbon atoms such as vinyl, allyl or butenyl;

"lower alkynyl" means unsaturated aliphatic hydrocarbon radicals comprising one or two triple bonds and having from 2 to 4 carbon atoms such as ethynyl, propargyl or butynyl;

"heterocyclic radical" designates more particularly a furyl, thienyl, pyrrolyl, benzofuryl, benzothienyl or indolyl radical.

Thus, taking the above-cited meanings into account, the Cy radical can more particularly represent an isobutyl-phenyl, preferably 4-isobutyl-phenyl or a chlorothienyl preferably 5-chloro-2-thienyl radical.

The compounds are particularly useful as intermediates in the synthesis of alkanoic acids of general formula:

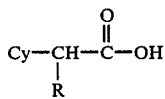

in which R and Cy have the same meaning as above.

Amongst these compounds, which are especially known as anti-inflammatory, antipyretic or antalgic agents the following may be cited: 2-(4-isobutyl-phenyl)-acetic acid or ibufenac, 2-(4-isobutyl-phenyl)-propionic acid or ibuprofen or 2-(4-isobutyl-phenyl)-butyric acid or butibufen.

The synthesis of ibuprofen from 2-(4-isobutyl-phenyl)-2-hydroxy-propionic acid as well as the preparation of this latter intermediate compounds has been described in Japanese Patent Application No. 54-39042 (C.A. 91, P140574u).

Following the process so described, the α-hydroxy-acid in question is prepared from ethyl 2-(4-isobutyl-phenyl)-2-oxo-acetate by reaction with a methyl magnesium halide in ether followed by alkaline hydrolysis in accordance with the conditions of the GRIGNARD reaction.

Though the yields obtained are considerable, the working conditions of such a reaction are expensive and difficult to carry out on the industrial scale (use of magnesium, anhydrous reaction medium etc . . . ).

Other publications also report processes of preparation of α-hydroxy-alkanoic acids of formula (I').

In most cases, these processes present disadvantages which preclude their use on the industrial scale.

These disadvantages can for instance be due to the use of starting products which are relatively difficult to obtain.

However, a process of preparation of certain α-hydroxy-phenylalkanoic acids is known involving working conditions which can be extrapolated without any major difficulty on the industrial scale.

This process, which is described in J.A.C.S. 72, 1642–1644 (1950) or in Org. Synth. III, 538–541 (1955) is based on a transposition reaction of α,α-dihalogenated phenylalkyl ketones involving the use of aqueous sodium hydroxide.

Attempts have been made to prepare acids of formula I and in particular 2-(4-isobutyl-phenyl)-2-hydroxy-propionic acid following such a method but with little succes.

The highest yields obtained in the desired acid were only about 19%, 4-isobutyl-benzoic acid being the product most frequently synthetized. In consequence, the preparation of α-hydroxy-phenylalkanoic acids of formula I following a process which can be used in industry remains or paramount importance.

It has now been found, in accordance with the invention, that the α-hydroxy-acids of formula I can be prepared on the industrial scale by means of a transposition reaction of α,α-dihalogenated ketones using an alkali metal hydroxide in aqueous solution and a non-polar organic solvent.

Thus, the process of the invention for the preparation of the α-hydroxy-alkanoic acids in question consists in:

treating an α,α-dihalogenated ketone of general formula:

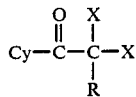

in which R and Cy have the same meaning as above and X represents chlorine, bromine or iodine, in the presence of an aqueous solution of an alkali metal hydroxide such as lithium, sodium or potassium hydroxide and a non-polar organic solvent selected from an aromatic or alicyclic hydrocarbon, treatment being carried out at a temperature ranging from the boiling temperature of the reaction medium at atmospheric pressure to 240° C. under pressure, then acidifying the alkali metal salt so formed to obtain the desired acid.

In the particular case of 2-(4-isobutyl-phenyl)-2-hydroxy-propionic acid, yields of 70 to 90% can be obtained by the process of the invention with less benzoic acid derivatives being produced by a side-reaction.

As aromatic hydrocarbon, toluene, xylenes, isobutyl-benzene or naphthalene can be used and, as alicyclic hydrocarbon, cyclohexane can, for instance, be employed. Generally xylenes are preferred and in particular industrial xylene for reasons of economy.

At atmospheric pressure and at the boiling temperature of the reaction medium, the transposition reaction is performed in 20 to 25 hours providing yields of at least 70%.

The non-limitative working conditions given below are usually utilized:
0.5 to 40 parts by weight of alkali metal hydroxide
5 to 400 parts by volume of water
2 to 40 parts by volume of organic solvent
these proportions being used for 1 part by weight of ketone of formula II, the reaction being carried out at the boiling temperature of the mixture so formed.

It has been found, in particular, that the transposition reaction of the invention can be considerably accelerated by increasing the temperature.

It has, in fact, been observed that an increase in the reaction temperature, preferably to between 160° and 240° C., which necessitates operating under pressure, produces the same effect as an increase in the duration of the reaction.

Thus, at a temperature ranging from 180° to 220° C., the transposition reaction in the reaction medium maintained under stirring and pressure, for instance by using a bomb-apparatus, can be performed in minutes for instance in 15 to 60 minutes.

At those temperatures between the boiling temperature of the reaction medium at atmospheric pressure and 240° C. under pressure, the following non-limitative working conditions are generally used:
0.5 to 10 parts by weight of an alkali metal hydroxide
5 to 150 parts by volume of water
1 to 30 parts by volume of organic solvent
these proportions being used for 1 part by weight of ketone of formula II.

In addition, it has been observed that at temperatures superior to the boiling temperature of the medium, the transposition reaction of the invention provides particularly high yields in alkali metal salts of α-hydroxy-acids of formula I.

At 160° C., 180° C., 200° C. and 220° C., the reaction does not produce more than 8% of benzoic acid derivative but yields as much as 90% in α-hydroxy-acid of formula I.

In accordance with a first manner of applying the process of the invention at a temperature between the boiling temperature of the reaction medium at atmospheric pressure and 240° C. under pressure, the alkali metal hydroxide in solution, xylene and dihalogenated ketone of formula II are mixed in the bomb-apparatus which is then closed and heated to the desired temperature.

A second mode of operation can also be used which consists in:
first introducing into the bomb-apparatus the aqueous solution of alkali metal hydroxide as well as the xylene if the dihalogenated ketone of formula II is liquid,
heating the bomb-apparatus when closed to obtain the desired temperature and, using a dispensing pump, introducing the dihalogenated ketone of formula II as such or dissolved in xylene.

Generally, the introduction of the dihalogenated ketone is performed in about 2 hours.

The productivity in α-hydroxy acid of formula I can be considerably increased, using the above working conditions, by adding the dihalogenated ketone in a continuous operation, this productivity in some cases being as high as 7% (7 g/100 ml) of the reaction medium.

The separation and purification of the α-hydroxy-acids of formula I can be obtained by precipitating the metal salts thereof from the reaction medium and then acidifying. Using these operating conditions, the acidification of the total mixture containing the base in excess can be avoided together with the extraction of the α-hydroxy-acids in question from a considerable volume of water.

Moreover, when the metal salts of the α-hydroxy-acids are precipitated the other acid impurities together with the sodium halides formed are not included in the precipitate but remain, owing to their greater solubility, almost entirely in the reaction medium and in the water.

These α-hydroxy-acid salts can therefore be removed by filtration.

This constitutes an undeniable advantage as the subsequent reactions, leading to the alkanoic acids of formula (I'), produce no or very few impurities.

The alkanoic acids in pure form can thus be obtained by a simple operation of purification of the starting-products namely the α-hydroxy-alkanoic acids of formula I.

In contrast with this, other prior processes only enable purification to be carried out at the level of the alkanoic acid, an operation which has been found to be difficult at this stage.

Another advantage of the process of the invention lies in the fact of being able to use starting compounds which are particularly valuable because very easily produced i.e. the compounds of formula II.

These compounds of formula II can be obtained, for instance, from a ketone of general formula:

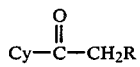
                              III in which R and Cy have the same meaning as above either by chloration with chlorine in N,N-dimethylformamide at 80°–100° C. in accordance with the method described in Synth. Commun., 9, 575–582 (1979) or by the action of bromine in excess in acetic acid in accordance with the method cited in Organic Syntheses, IV, 110–113 (1963), the ketone of formula III being itself produced from a compound of formula Cy-H in which Cy has the same meaning as above, by Friedel-Crafts reaction with acyl chlorides of general formula:

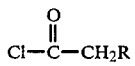
                              IV in which R has the same meaning as above.

As an alternative procedure, the compounds of formula II in which Cy represents a phenyl radical as defined in formula I can be directly obtained by acylation, following the conditions of the Friedel-Crafts reaction, by means of α,α-dihalogenated acyl halides of general formula:

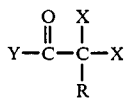
                              V in which R and X have the same meaning as above and Y represents chlorine or bromine, or by means of anhydrides or other equivalents derivatives of the above compounds of formula V.

As mentioned above, the α-hydroxy-alkanoic acids of formula I can be used as intermediate products for the preparation of the alkanoic acids of formula (I') above.

For this purpose, the compounds of formula I will be used following procedures such as:

(a) Dehydration under reflux in a solvent by means, for instance, of p-toluene-sulphonic acid followed by catalytic hydrogenation in a solvent of the 2-alkenoic acid obtained, by applying the method described in Patent Application No. 2,613,817 of the Federal Republic of Germany.

(b) Hydrogenolysis of the α-hydroxy-acids, for instance in the presence of RANEY's nickel in acetic acid at 170° C. and under 16 atmospheres as described in Japanese Patent Application No. 53-02449 (C.A. 89, 6118d) or in the presence of palladium charcoal in acetic acid at 60° C. and under 30 atmospheres as described in Japanese Patent Application No. 53-34745 (C.A. 89, 108684e).

Alterations to the above prior methods can also be made by using either palladium charcoal or sulphuric acid as catalyst and thus operating at atmospheric pressure or by using hydriodic acid in acetic acid.

As mentioned above, the process of the invention has been found to be far superior to the processes suggested by the prior art involving transposition reactions of α,α-dihalogenated ketones.

To this end, trials aimed at the transposition of 2,2-dichloro-1-(4-isobutyl-phenyl)-1-propanone to 2-(4-isobutyl-phenyl)-2-hydroxy-propionic acid were carried out on the one hand following the process of the invention and on the the other following prior art conditions.

The results given hereunder were obtained:

(a) In accordance with the invention:

| Reagents and solvent for 1 g of ketone | | | Transposition reaction | | Molar yields (%) | |
|---|---|---|---|---|---|---|
| NaOH (g) | Water (ml) | Xylene (ml) | Temperature | Duration (h) | A* | B** |
| 20 | 400 | 40 | Boiling | 24 | 85 | 2 |
| 20 | 200 | 40 | Boiling | 24 | 75 | 3 |

(b) In accordance with prior art conditions:

| Working conditions | Molar yields (%) | |
|---|---|---|
| | A* | B** |
| NaOH 20%/water/20° C./29 h | 0 | 7 |
| NaOH 20%/water/60° C./2.5 h + ethanol/1 additional hour | 0 | 33 |
| NaOH 32%/water/20° C./6 h + ethyleneglycol + ethanol/1 h. | 19 | 40 |

*2-(4-isobutyl-phenyl)-2-hydroxy-propionic acid
**4-isobutyl-benzoic acid

These results show the marked superiority of the process of the invention as regards high yield in α-hydroxy-acid formed and the small proportion of 4-isobutyl-benzoic acid formed by a side-reaction.

The following non-limitative Examples illustrate the process of the invention:

EXAMPLE 1

Preparation of 2-(4-isobutyl-phenyl)-2-hydroxy-propionic acid (a) 1-(4-Isobutyl-phenyl)-1-propanone In 30 minutes at 20°–25° C. were added 102 g (1.1 mol) of propionyl chloride to a suspension of 140 g (1.05 mol) of aluminium chloride in 540 ml of anhydrous methylene chloride. A pale yellow solution was obtained to which 134 g (1 mol) of isobutyl-benzene were added in 25 minutes at 20°–25° C.

The reaction medium was stirred for 90 minutes at 20°–25° C. and then 500 ml of 10%-hydrochloric acid were introduced without going beyond 25° C. by cooling with an iced water bath. After decantation, the aqueous phase was extracted with methylene chloride. The organic phases were washed with saline water, dried on sodium sulphate and brought to dryness under vacuum. The crude product was distilled under vacuum.

In this manner, 179 g of 1-(4-isobutyl-phenyl)-1-propanone were obtained titrating 95.9% in gaseous phase chromatography (G.P.C.) corresponding to a molar yield of 90.2%.

B.P.: 100°–103° C. under 0.2 mm Hg

An analytical sample of this derivative was prepared by preparation chromatography on silica plate with hexane containing 4% ethyl acetate as eluent.

G.P.C.: 99.7%

| Analysis | | | | |
|---|---|---|---|---|
| C | calculated | 82.06% | found | 81.46% |
| H | calculated | 9.54% | found | 9.17% |

I.R. (film) 1675, 1610, 780 cm$^{-1}$
N.M.R. (CCl$_4$) 7.80 and 7.15 (2d, 4H); 2.90 (q, 2H); 2.50 (d, 2H); 1.90 (m, 1H); 1.15 (t, 3H); 0.90 ppm (d, 6H)
n$_D^{22}$: 1.5145

Proceeding as described above with butyryl chloride in place of propionyl chloride, there were obtained 193.5 g of 1-(4-isobutyl-phenyl)-1-butanone titrating 95.2% in G.P.C. namely a molar yield of 90.3%.

B.P.: 115°–119° C. under 1 mm Hg

An analytical sample of this derivative was prepared by distillation.

P.E.: 117°–119° C. under 1 mm Hg
G.P.C.: 97.5%

| Analysis | | | | |
|---|---|---|---|---|
| C | calculated | 82.30% | found | 81.95% |
| H | calculated | 9.87% | found | 9.94% |

I.R. (film) 3100–3000, 1680, 1600–1570 cm$^{-1}$
N.M.R. (CDCl$_3$) 7.90 and 7.30 (2d, 4H); 3.00 (t, 2H); 2.60 (d, 2H); 2.00–1.50 (m, 3H); 1.00 ppm (d and t, 9H).
n$_D^{22}$: 1.5095

(b) 2,2-Dichloro-1-(4-isobutyl-phenyl)-1-propanone

In a solution of 190 g (1 mol) of 1-(4-isobutyl-phenyl)-1-propanone (G.P.C.: 96.9%) in 950 ml of anhydrous N,N-dimethylformamide, chlorine was bubbled for 5.66 hours at 90±5° C.

The chlorine in excess was eliminated with nitrogen and the medium was evaporated to dryness under vacuum. The residue was taken up in water and the whole was extracted with ethyl ether.

The organic phases were washed with water, dried and brought to dryness under vacuum.

In this manner, 248.7 g of 2,2-dichloro-1-(4-isobutyl-phenyl)-1-propanone were obtained titrating 96.4% in G.P.C. namely a molar yield of 95.4%.

B.P.: 156°–158° C. under 20 mm Hg

Chlorine: 25.9–25.94% (theory: 27.35%) i.e. a titration of 94.7%.

I.R. (film) 1690, 1610 cm$^{-1}$

N.M.R. (CDCl$_3$) 8.3 and 7.25 (2d, 4H); 2.5 (d, 2H); 2.3 (s, 3H); 1.9 (m, 1H); 0.9 ppm (d, 6H).

| Analysis | | | | |
|---|---|---|---|---|
| C | calculated | 60.25% | found | 60.07% |
| H | calculated | 6.22% | found | 6.09% |
| Cl | calculated | 27.36% | found | 27.59% |

(1) Proceeding as described above from 1-(4-isobutyl-phenyl)-1-ethanone, 2,2-dichloro-1-(4-isobutyl-phenyl)-1-ethanone was obtained in a molar yield of 79.8%. An analytical sample was prepared by recrystallisation from a hexane/toluene 1:2 mixture.

M.P.: 73° C.

G.P.C.: 99.9%

Chlorine: 28.78–28.62% (theory: 28.92%) i.e. a titration of 99.5%

I.R. 3100–3000, 1690, 1600–1570 cm$^{-1}$

N.M.R. (CDCl$_3$) 8 and 7.3 (2d, 4H); 6.7 (s, 1H); 2.55 (d, 2H); 1.9 (m, 1H); 0.95 ppm (d, 6H)

| Analysis | | | | |
|---|---|---|---|---|
| C | calculated | 58.79% | found | 59.12% |
| H | calculated | 5.76% | found | 5.85% |
| Cl | calculated | 28.92% | found | 28.42% |

(2) Proceeding as above from 1-(4-isobutyl-phenyl)-1-butanone, 2,2-dichloro-1-(4-isobutyl-phenyl)-1-butanone was obtained in a molar yield of 97.6%. An analytical sample was prepared by distillation under vacuum.

B.P.: 134°–135° C. under 1.2 mm Hg

G.P.C.: 96.3%

Chlorine: 25.9–26.0% (theory: 25.95%) i.e. a titration of 100%

I.R. 1685, 1600–1570, 860 cm$^{-1}$

N.M.R. (CDCl$_3$) 8.20 and 7.20 (2d, 4H); 2.50 (m, 4H); 2.00 (m, 1H); 1.30 (t, 3H); 0.90 ppm (d, 6H)

| Analysis | | | | |
|---|---|---|---|---|
| C | calculated | 61.55% | found | 61.05% |
| H | calculated | 6.64% | found | 6.58% |
| Cl | calculated | 25.95% | found | 25.75% |

$n_D^{22}$: 1.5305

(c) 2-(4-Isobutyl-phenyl)-2-hydroxy-propionic acid

Into a 500 ml-bomb-apparatus, were introduced 2 g (7.7×10$^{-3}$ mol) of 2,2-dichloro-1-(4-isobutyl-phenyl)-1-propanone (G.P.C.: 95.4%), 7.2 g (0.18 mol) of sodium hydroxide in pellets, 200 ml of water and 40 ml of xylene. The mixture was brought to 200° C. and stirred for 1 hour at this temperature. The inner pressure in the bomb-apparatus was about 14 bars. After cooling at 20° C., the medium was decanted and the aqueous phases were re-extracted with ethyl ether. After acidification at pH=1 with concentrated hydrochloric acid, the medium was again extracted with ethyl ether. These last ethereal phases were washed with water, dried on sodium sulphate and brought to dryness under vacuum. In this manner, 1.60 g of 2-(4-isobutyl-phenyl)-2-hydroxy-propionic acid were obtained titrating 91.6% in G.P.C. namely a molar yield of 89.8%. An analytical sample was prepared by crystallisation from hexane.

G.P.C.: 99.2%

M.P.: 106° C.

Acidimetric titration: 99.4%

I.R. (KBr) 3420, 3300–2500, 1735 cm$^{-1}$

N.M.R. (CDCl$_3$) 7.6 (m, 2H); 7.4 and 7.05 (2d, 4H); 2.45 (d, 2H); 1.75 (s+m, 4H); 0.9 ppm (d, 6H).

| Analysis | | | | |
|---|---|---|---|---|
| C | calculated | 70.24% | found | 70.63% |
| H | calculated | 8.16% | found | 8.18% |

Proceeding as described above, the following compounds were prepared:

(1) From 2,2-dichloro-1-(4-isobutyl-phenyl)-1-ethanone, 2-(4-isobutyl-phenyl)-2-hydroxy-acetic acid was obtained in a molar yield of 86.8%. An analytical sample was obtained by recrystallisation from hexane.

M.P.: 138° C.

G.P.C.: 99.6%

Acidimetric titration: 99.6%

I.R. 3420, 3200–2500, 1710 cm$^{-1}$

N.M.R. (CDCl$_3$) 7.15 (m, 6H); 5 (s, 1H); 2.4 (d, 2H); 1.85 (m, 1H); 0.85 ppm (d, 6H).

| Analysis | | | | |
|---|---|---|---|---|
| C | calculated | 69.21% | found | 69.14% |
| H | calculated | 7.74% | found | 7.76% |

(2) From 2,2-dichloro-1-(4-isobutyl-phenyl)-1-butanone, 2-(4-isobutyl-phenyl)-2-hydroxy-butanoic acid was obtained in a molar yield of 80.9%. An analytical sample was prepared by recrystallisation in hexane.

G.P.C.: 99.3%

M.P.: 117° C.

Acidimetric titration: 99.2%

I.R. 3420, 3100–2700, 1720 cm$^{-1}$

N.M.R. (CDCl$_3$) 7.5 and 7.1 (2d+m, 6H); 2.45 (d, 2H); 2.1 (m, 3H); 0.9 ppm (t+d, 9H).

| Analysis | | | | |
|---|---|---|---|---|
| C | calculated | 71.16% | found | 71.25% |
| H | calculated | 8.53% | found | 8.64% |

Other trials were carried out for the preparation of 2-(4-isobutyl-phenyl)-2-hydroxy-propionic acid (A) by varying the amounts of sodium hydroxide, water and xylene as well as the temperature and the duration of the reaction.

| Reagents for 2 g of dichloroketone | | | Transposition reaction | | Molar yields (in %) | |
|---|---|---|---|---|---|---|
| NaOH (g) | water (ml) | xylene (ml) | Temperature (°C.) | Duration (h) | A | B |
| 7.2 | 150 | 30 | 180 | 0.25 | 77 | 7 |
| 10 | 200 | 40 | 200 | 1 | 92 | 4 |
| 7.2 | 200 | 40 | 200 | 1 | 86 | 4 |
| 7.2 | 100 | 20 | 200 | 1 | 69 | 4 |
| 7.2 | 200 | 40 | 200 | 0.25 | 90 | 4 |
| 7.2 | 120 | 20 | 200 | 0.25 | 78 | 13 |
| 7.2 | 150 | 30 | 200 | 0.25 | 84 | 8 |

| Reagents for 2 g of dichloroketone | | | Transposition reaction | | Molar yields (in %) | |
|---|---|---|---|---|---|---|
| NaOH (g) | water (ml) | xylene (ml) | Temperature (°C.) | Duration (h) | A | B |
| 7.2 | 200 | 40 | 200 | 0.25 | 88 | 4 |
| 3.6 | 200 | 40 | 200 | 1 | 82 | 6 |

EXAMPLE 2

Preparation of 2-(4-isobutyl-phenyl)-2-hydroxy-acetic acid (a) 2,2-Dibromo-1-(4-isobutyl-phenyl)-1-ethanone A solution of 8 g (0.05 mol) of bromine in 10 ml of acetic acid was added while stirring, in 1 hour at 40° C., to a solution of 8.8 g (0.05 mol) of 1-(4-isobutyl-phenyl)-1-ethanone (G.P.C.: 94.5%) in 30 ml of acetic acid. The reaction medium was stirred for a further 3 hours at 80° C., cooled to 20° C. and then poured into water. After extraction with ethyl ether, the organic phases were washed with water, dried and evaporated.

In this manner, 14.83 g of 2,2-dibromo-1-(4-isobutyl-phenyl)-1-ethanone were obtained titrating 77.3% in G.P.C. namely a molar yield of 72.6%.

An analytical sample was prepared by recrystallisation from petroleum ether.

M.P.: 68° C.
G.P.C.: 97.7%
Bromine: 47.22–47.29% (theory: 47.84%) namely a titration of 98.8%.
I.R. 3100–3000, 1680, 1600–1570, 850 cm$^{-1}$
N.M.R. (CDCl$_3$) 7.95 and 7.25 (2d, 4H); 6.7 (s, 1H); 2.55 (d, 2H); 1.9 (m, 1H); 0.9 ppm (d, 6H).

| Analysis | | | | |
|---|---|---|---|---|
| C | calculated | 43.15% | found | 43.02% |
| H | calculated | 4.22% | found | 4.17% |
| Br | calculated | 47.26% | found | 47.84% |

Proceeding as described above from 1-(4-isobutyl-phenyl)-1-propanone, 2,2-dibromo-1-(4-isobutyl-phenyl)-1-propanone was obtained in the form of a colourless oil in a molar yield of 52.5%.

An analytical sample was prepared by chromatography on a silica column, 70–230 mesh with hexane as eluent.

G.P.C.: 98.2%
I.R. (film) 1675, 1600–1570, 860 cm$^{-1}$
N.M.R. (CDCl$_3$) 8.40 and 7.20 (2d, 4H); 2.75 (s, 3H); 2.60 (d, 2H); 2.20–1.50 (m, 1H); 0.90 ppm (d, 6H)
n$_D^{20}$: 1.5665

| Analysis | | | | |
|---|---|---|---|---|
| C | calculated | 44.56% | found | 44.95% |
| H | calculated | 4.63% | found | 4.64% |
| Br | calculated | 45.91% | found | 46.74% |

(b) 2-(4-Isobutyl-phenyl)-2-hydroxy-acetic acid

Proceeding as in Example 1c but from 2,2-dibromo-1-(4-isobutyl-phenyl)-1 ethanone, 2-(4-isobutyl-phenyl)-2-hydroxy-acetic acid was obtained in a molar yield of 93.6%.

Similarly, following the method of Example 1c, 2-(4-isobutyl-phenyl)-2-hydroxy-propionic acid was obtained in a molar yield of 89.6% from 2,2-dibromo-1-(4-isobutyl-phenyl)-1-propanone.

EXAMPLE 3

Preparation of 2-(4-isobutyl-phenyl)-2 hydroxy-propionic acid

Into a flask, there were introduced 1 g of 2,2-dichloro-1-(4-isobutyl-phenyl)-1-propanone, the alkali metal hydroxide, a varying quantity of water and 40 ml of a non-polar organic solvent.

The mixture was brought to the boil and maintained at this temperature under stirring for 24 hours.

After cooling to 20° C., the medium was decanted and the aqueous phases were extracted with ethyl ether. After acidification to pH=1 with concentrated hydrochloric acid, the mixture was again extracted with ethyl ether. These latter phases were washed with water, dried on sodium sulphate and brought to dryness under vacuum.

In this manner, 2-(4-isobutyl-phenyl)-2-hydroxy-propionic acid (A) was obtained.

The following yields in this product (A) were registered in comparison with 4-isobutyl-benzoic acid (B) taking into account the cited working conditions.

(a) Alkali metal hydroxide: NaOH

| Conditions | | | Molar yields (%) | |
|---|---|---|---|---|
| NaOH (g) | H$_2$O (ml) | Solvent | A | B |
| 40 | 400 | xylene | 67 | |
| 40 | 200 | xylene | 71 | 11 |
| 20 | 400 | xylene | 85 | 2 |
| 20 | 200 | xylene | 75 | 3 |
| 10 | 200 | xylene | 74 | 3 |
| 10 | 400 | xylene | 74 | 4 |
| 40 | 400 | toluene | 61 | 1.5 |
| 40 | 400 | isobutylbenzene | 93 | 3.5 |
| 40 | 400 | naphthalene | 68 | 10.5 |
| 40 | 400 | cyclohexane | 78 | 6 |

(b) Alkali metal hydroxide: KOH

| Conditions | | | Molar yields (%) | |
|---|---|---|---|---|
| KOH (g) | H$_2$O (ml) | Solvent | A | B |
| 40 | 400 | xylene | 91 | 0 |

(c) Alkali metal hydroxide: LiOH

| Conditions | | | Molar yields (%) |
|---|---|---|---|
| LiOH (g) | H$_2$O (ml) | Solvent | A |
| 40 | 400 | xylene | 87 |

EXAMPLE 4

Preparation of 2-(4-isobutyl-phenyl)-2-hydroxy-propionic acid

Into a 2 l stainless-steel bomb-apparatus, fitted with a central mechanical stirrer, were introduced 180 ml of industrial xylene, 900 ml of water and 86.4 g (2.16 mols) of sodium hydroxide in pellet form.

The apparatus was closed and the inner temperature was brought to 180° C. By means of a pump, 119.6 g (0.439 mol) of 2,2-dichloro-1-(4-isobutyl-phenyl)-1-propanone (G.P.C.: 95.2%) were added in 2 hours, stirring being maintained and the temperature kept at 180° C. The medium was stirred and heated for a further 15 minutes after the operation of introduction was terminated and then the apparatus was cooled in a current of air.

To the reaction mass, cooled to 20° C., 200 g of sodium chloride were added and the whole was stirred for 1 hour and filtered on fritted glass. The precipitate was washed with ethyl acetate and then taken up in 1080 ml of water. The suspension so obtained was acidified with 40 ml of concentrated hydrochloric acid and then filtered. The precipitate so obtaind was washed with water and dried at 50° C. under 5 mm Hg.

In this manner, 84.54 g of crude 2-(4-isobutyl-phenyl)-2-hydroxy-propionic acid were isolated titrating 94.3% in G.P.C. corresponding to a molar yield of 81.7%.

EXAMPLE 5

Preparation of 2-(5-chloro-2-thienyl)-2-hydroxy-propionic acid (a) 2,2-Dichloro-1-(5-chloro-2-thienyl)-1-propanone Chlorine was bubbled for 2 h at 90°-100° C. in a solution of 10 g ($70 \times 10^{-3}$ mol) of 2-propionyl-thiophene in 40 ml of anhydrous N,N-dimethylformamide.

After eliminating the chlorine in excess with nitrogen, the N,N-dimethylformamide was evaporated off under vaccum and the residue was taken up in water and extracted with ethyl ether.

The organic phases were washed with saline water, dried on sodium sulphate and brought to dryness under vacuum.

In this manner, 16.76 g of 2,2-dichloro-2-(5-chloro-2-thienyl)-1-propanone were obtained titrating 40.2% in G.P.C. namely a molar yield of 39.5%.

An analytical sample was prepared by distillation under vacuum and further crystallisation from hexane.

M.P.: 50° C.
G.P.C.: 96.5%
I.R. (KBr): 1660 cm$^{-1}$
N.M.R. (CDCl$_3$) 8.00 (d, 1H); 7.00 (d, 1H); 2.30 ppm (s, 3H)

|   | Analysis | | | |
|---|---|---|---|---|
| C | calculated | 34.52% | found | 34.42% |
| H | calculated | 2.07% | found | 2.02% |
| Cl | calculated | 43.68% | found | 43.91% |

(b) 2-(5-Chloro-2-thienyl)-2-hydroxy-propionic acid

In a 2l stainless-steel bomb-apparatus, equipped with a central mechanical stirrer, were placed 120 ml of water, 4.32 g ($108 \times 10^{-3}$ mol) of sodium hydroxide in pellet form, 1.164 g ($4.42 \times 10^{-3}$ mol) of 2,2-dichloro-1-(5-chloro-2-thienyl)-1-propanone and 24 ml of xylene.

The apparatus was closed and the inner temperature was brought to 200° C. The reaction medium was stirred for 15 minutes at 200° C. and the apparatus was then cooled in a current of air. The medium was extracted with ethyl ether and the aqueous phase was acidified to pH=1 with concentrated hydrochloric acid. After a further extraction with ethyl ether, these latter organic phases were washed with saline water, dried on sodium sulphate and brought to dryness under vacuum.

In this manner, 0.89 g of 2-(5-chloro-2-thienyl)-2-hydroxy-propionic acid was obtained titrating 84.3% in G.P.C., namely a molar yield of 82.2%.

An analytical sample was prepared by recrystallisation from toluene.

M.P.: 93° C.
G.P.C.: 95.4%
I.R. (KBr) 3390, about 2950 large, 1725 cm$^{-1}$
N.M.R. (CDCl$_3$) 8.20 (m, 2H); 7.00-6.70 (m, 2H); 1.75 ppm (s, 3H).

|   | Analysis | | | |
|---|---|---|---|---|
| C | calculated | 40.69% | found | 40.23% |
| H | calculated | 3.41% | found | 3.43% |
| S | calculated | 15.52% | found | 15.30% |
| Cl | calculated | 17.16% | found | 17.61% |

EXAMPLE 6

Preparation of 2-hydroxy-2-phenyl-propionic acid (a) 2,2-Dichloro-1-phenyl-1-propanone Chlorine was bubbled for 1.25 h at 100° C. in a solution of 33.5 g (0.25 mol) of propiophenone in 300 ml of anhydrous N,N-dimethylformamide. The reaction medium was cooled to 20° C. and poured into 600 ml of 2N-hydrochloric acid. After extraction with ethyl ether, the organic phases were washed with water, dried and brought to dryness under vacuum.

In this manner, 49.6 g of 2,2-dichloro-1-phenyl-1-propanone were obtained having a chlorine titration of 96.4%, namely a molar yield of 94.2%.

After distillation a product was obtained having the following characteristics:

I.R. (film) 1700, 1605 cm$^{-1}$
N.M.R. (CCl$_4$) 8.30 and 7.45 (2m, 5H); 2.30 ppm (s, 3H).

Chlorine: calculated: 34.9% found: 34.0% namely a titration of 97.4%

(b) 2-Hydroxy-2-phenyl-propionic acid

Proceeding as described in Example 5 from 2 g ($9.6 \times 10^{-3}$ mol) of 2,2-dichloro-1-phenyl-1-propanone, there were obtained 1.42 g of 2-hydroxy-2-phenyl-propionic acid titrating 54.4% in G.P.C. namely a molar yield of 48.5%.

An analytical sample was prepared by recrystallisation from isopropyl ether.

M.P.: 84° C.
G.P.C.: 97.6%
I.R. (KBr) 3480, 3280, about 2900 large, 1710 cm$^{-1}$
N.M.R. (DMSOd$_6$); 7.80-7.20 (m, 7H); 1.75 ppm (s, 3H).

The following Examples illustrate the preparation of alkanoic acids of formula (I') from α-hydroxy-acids of formula I.

EXAMPLE I

Preparation of 2-(4-isobutyl-phenyl)-propionic acid from the corresponding compound of formula I (a) 2-(4-Isobutyl-phenyl)-propenoic acid.

A solution of 2.22 g ($9.7 \times 10^{-3}$ mol) of 2-(4-isobutyl-phenyl)-2-hydroxy-propionic acid (G.P.C.: 96.9%) and 2.22 g of monohydrated p-toluenesulphonic acid in 90 ml of benzene was stirred for 2 hours under reflux (while eliminating water by azeotropy). After cooling to 20° C., the medium was washed with saline water, dried on sodium sulphate and brought to dryness under vacuum.

In this manner, 1.98 g of 2-(4-isobutyl-phenyl)-propenoic acid were obtained titrating 98.8% in G.P.C. namely a molar yield of 99.0%.

An analytical sample was prepared by recrystallisation from hexane.

M.P.: 95° C.
G.P.C.: 100%
I.R. (KBr) 3300–2500, 1670, 1615–1605, 840 cm$^{-1}$
N.M.R. (CDCl$_3$) 11.9 (s, 1H); 7.2 (m, 4H); 6.5 and 5.95 (2s, 2×1H); 2.45 (d, 2H); about 1.8 (m, 1H); 0.9 ppm (d, 6H).

| Analysis | | | | |
|---|---|---|---|---|
| C | calculated | 76.44% | found | 76.27% |
| H | calculated | 7.90% | found | 7.88% |

Proceeding as above from 2-(4-isobutyl-phenyl)-2-hydroxy-butanoic acid, 2-(4-isobutyl-phenyl)-2-butenoic acid was obtained in a molar yield of 91.9%.

An analytical sample was prepared by recrystallisation from hexane.
G.P.C.: 96.4%
M.P.: 47° C.
I.R. About 3000 cm$^{-1}$, 1695 cm$^{-1}$
N.M.R. (CDCl$_3$) 12.3 (s, 1H); 7.3–6.95 (m, 4H); 6.35 (q, 1H); 2.45 (d, 2H); 2.1 (d, 2H); 1.9 (m, 1H); 0.9 ppm (d, 6H)

| Analysis | | | | |
|---|---|---|---|---|
| C | calculated | 77.03% | found | 76.67% |
| H | calculated | 8.31% | found | 8.27% |

(b) 2-(4-Isobutyl-phenyl)-propionic acid

A suspension of 0.80 g (3.9×10$^{-3}$ mol) of 2-(4-isobutyl-phenyl)-propenoic acid and 40 mg of 5%-palladium charcoal in 16 ml of ethanol was stirred for 1.25 hour at 20° C. under hydrogen atmosphere. After filtration of the catalyst, the reaction medium was brought to dryness under vacuum.

In this manner, 0.80 g of 2-(4-isobutyl-phenyl)-propionic acid or ibuprofen was obtained titrating 98.1% in G.P.C. namely a molar yield of 97.1%.
M.P.: 78° C.
I.R. About 3000, 1710 cm$^{-1}$
N.M.R. (CDCl$_3$) 9.95 (s, 1H); 7.1 (m, 4H); 3.65 (q, 1H); 2.45 (d, 2H); 1.95 (m, 1H); 1.45 (d, 3H); 0.9 ppm (d, 6H).

Proceeding as described above from 2-(4-isobutyl-phenyl)-2-butenoic acid, 2-(4-isobutyl-phenyl)-butanoic acid or butibufen was obtained in a yield of 100%.
I.R. About 3000, 1705 cm$^{-1}$
N.M.R. (CDCl$_3$) 11.25 (s, 1H); 7.1 (m, 4H); 3.4 (t, 1H); 2.45 (d, 2H); 2.2–1.5 (m, 3H); 0.9 ppm (d+t, 9H).

| Analysis | | | | |
|---|---|---|---|---|
| C | calculated | 76.33% | found | 76.28% |
| H | calculated | 9.15% | found | 9.30% |

EXAMPLE II

Preparation of 2-(4-isobutyl-phenyl)-propionic acid from the corresponding compound of formula I A suspension of 2.22 g (9.7×10$^{-3}$ mol) of 2-(4-isobutyl-phenyl)-2-hydroxy-propionic acid (G.P.C.: 96.9%), 0.44 g of 5%-palladium charcoal in 20 ml of acetic acid and 2.2 ml of sulphuric acid was stirred, for 29 hours at 20° C., under hydrogen atmosphere. The reaction medium was filtered and water was added. After extraction with ethyl ether, the organic phases were washed with water, dried on sodium sulphate and brought to dryness under vacuum.

In this manner, 2.05 g of 2-(4-isobutyl-phenyl)-propionic acid or ibuprofen were obtained titrating 88% in G.P.C. namely a molar yield of 90.4%.

(a) Proceeding as above from 2-(4-isobutyl-phenyl)-2-hydroxy-acetic acid, 2-(4-isobutyl-phenyl)-acetic acid or ibufenac was obtained in a molar yield of 95.3%. An analytical sample was prepared by recrystallisation from hexane.
G.P.C.: 99.7%
M.P.: 85° C.
I.R. (KBr) 3500–2500, 1695 cm$^{-1}$
N.M.R. (CDCl$_3$) 11.95 (s, 1H); 7.1 (m, 4H); 3.6 (s, 2H); 2.45 (d, 2H); 1.95 (m, 1H); 0.9 ppm (d, 6H).

| Analysis | | | | |
|---|---|---|---|---|
| C | calculated | 74.97% | found | 75.38% |
| H | calculated | 8.39% | found | 8.47% |

(b) Proceeding as above from 2-(4-isobutyl-phenyl)-2-hydroxy-butanoic acid, 2-(4-isobutyl-phenyl)-butanoic acid or butibufen was obtained in a molar yield of 83.1%.

EXAMPLE III

Preparation of 2-(4-isobutyl-phenyl)-propionic acid from the corresponding compound of formula I A solution of 2.22 g (9.7×10$^{-3}$ mol) of 2-(4-isobutyl-phenyl)-2-hydroxy-propionic acid (G.P.C.: 96.9%) in 13 ml of acetic acid and 4.4 ml of 57%-hydriodic acid was stirred for 6 hours at 60° C. The reaction medium was cooled to 20° C. and poured into a solution of sodium bisulphite. After extraction with ethyl ether, the organic phases were washed with water containing sodium chloride, dried on sodium sulphate and brought to dryness under vacuum.

In this manner 2.06 g of 2-(4-isobutyl-phenyl)-propionic acid were obtained titrating 91% in G.P.C. namely a yield of 93.9%.

We claim:
1. Process for preparing α-hydroxy-alkanoic acids of formula:

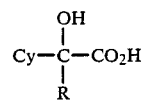

$$\text{Cy} - \underset{\underset{R}{|}}{\overset{\overset{OH}{|}}{C}} - CO_2H \qquad I$$

in which R represents a lower alkyl radical and Cy represents phenyl or a heterocyclic radical, both radicals optionally containing one or more subtituents selected from the group consisting of lower alkyl, lower alkenyl, lower alkynyl radicals and halogen atoms, wherein:

an α,α-dihalogenated ketone of formula:

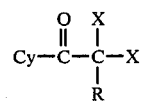

$$\text{Cy} - \underset{\underset{R}{|}}{\overset{\overset{O\ \ X}{||\ \ |}}{C - C}} - X \qquad II$$

in which R and Cy have the same meaning as above and X represents chlorine, bromine or iodine is treated in the presence of an aqueous solution of an alkali metal hydroxide and of a non polar organic solvent which is an aromatic or alicyclic hydrocarbon, the treatment being carried out at a temperature between the boiling temperature of the reaction medium at atmospheric pressure and 240° C. under pressure the alkali metal so formed is then acidified to obtain the desired acid.

2. A process according to claim 1 wherein the alkali metal hydroxide is lithium, sodium or potassium hydroxide.

3. A process according to claim 1 wherein the aromatic hydrocarbon is a xylene.

4. A process according to claim 1 wherein R represents methyl or ethyl.

5. A process according to claim 1 wherein Cy represents a 4-isobutyl-phenyl radical.

6. A process according to claim 1 wherein:
0.5 to 40 parts by weight of alkali metal hydroxide
5 to 400 parts by volume of water
2 to 40 parts by volume of solvent,
are used for 1 part by weight of $\alpha,\alpha$-dihalogenated ketone, the treatment being carried out at the boiling temperature of the reaction medium at atmospheric pressure.

7. A process according to claim 1 wherein:
0.5 to 10 parts by weight of alkali metal hydroxide
5 to 150 parts by volume of water
1 to 30 parts by volume of solvent,
are used for 1 part by weight of $\alpha,\alpha$-dihalogenated ketone, the treatment being carried out at a temperature between the boiling temperature of the reaction medium at atmospheric pressure and 240° C. under pressure.

8. A process according to claim 1 wherein the treatment is carried out at a temperature of 180° to 220° C.

9. A process according to claim 1 wherein the treatment is carried out in a bomb-apparatus at a temperature between the boiling temperature of the reaction medium at atmospheric pressure and 240° C. by introducing, in a continuous manner, the $\alpha,\alpha$-dihalogenated ketone into the said reaction medium.

* * * * *